United States Patent [19]

Lombard et al.

[11] 4,194,392
[45] Mar. 25, 1980

[54] MEASURING ADHESIVE FORCE

[75] Inventors: Serge Lombard, Les Ulis; Patrick Borg, Rueil Malmaison, both of France

[73] Assignee: ATO Chimie, Courbevoie, France

[21] Appl. No.: 905,150

[22] Filed: May 12, 1978

[30] Foreign Application Priority Data

Jun. 10, 1977 [FR] France .............................. 77 17808
Jan. 10, 1978 [FR] France .............................. 78 00495

[51] Int. Cl.$^2$ .............................................. G01N 3/08
[52] U.S. Cl. ...................................... 73/150 A; 73/827
[58] Field of Search .................. 73/150 R, 150 A, 827

[56] References Cited

U.S. PATENT DOCUMENTS

| 2,894,388 | 7/1959 | Cook et al. ............ 73/150 R X |
| 3,129,586 | 4/1964 | Allen et al. ............ 73/150 R X |
| 3,186,221 | 6/1965 | Steib ..................... 73/150 A |
| 3,253,461 | 5/1966 | Blanchard et al. ........ 73/150 A |
| 3,269,176 | 8/1966 | Egitto et al. ............ 73/150 A |
| 3,825,819 | 7/1974 | Hansen et al. ........... 73/150 A |
| 3,926,037 | 12/1975 | Kopito et al. ........... 73/150 A |

FOREIGN PATENT DOCUMENTS

| 2227525 | 10/1973 | France ................... 73/150 A |
| 528585 | 11/1940 | United Kingdom ........ 73/150 R |
| 542968 | 2/1942 | United Kingdom ........ 73/150 R |

Primary Examiner—Daniel M. Yasich
Attorney, Agent, or Firm—Burgess, Ryan and Wayne

[57] ABSTRACT

A process for measuring the adhesive power of pressure-sensitive adhesives, especially adhesive tapes or sheets; it is also related to a device for implementing this process. This process consists in causing a ball to fall freely onto the adhesive surface of the tape or sheet and exerting a vertical upwardly directed separating force upon the ball, the measurement of the adhesive power of the adhesive being a function of the time comprised between the instant when the separating force is initially exerted upon the ball and the instant when the ball returns to its initial starting point.

10 Claims, 4 Drawing Figures

MEASURING ADHESIVE FORCE

The present invention is related to a process for measuring the adhesive power of pressure-sensitive adhesives, especially adhesive tapes or sheets; it is also related to a device for implementing this process.

Various process for measuring adhesive power or surface adhesiveness have been proposed.

A well known process is that of dropping a ball from the top of an inclined plane of predetermined length and slope; the ball accelerates as it rolls down the plane, then rolls along a horizontal surface which extends from the lower edge of said inclined plane and which is covered with the adhesive, the adhesive power of which is to be measured. The adhesive power is determined by measuring the distance which the ball travels along the flat adhesive-covered surface.

The results obtained by this process are rather inconsistent.

Another known process is to bring a loop, formed by an adhesive tape, the adhesive surface being on the outside, into contact with a plate, in such a manner that the plate and loop are glued together, then to measure the force required to separate them. The results thus obtained are not consistent.

The object of the present invention is a process for measuring the surface adhesiveness of an adhesive which does not present the above-mentioned drawbacks and which, while being relatively simple, leads to consistent results.

The present invention concerns a process for determining the adhesive power of a pressure-sensitive adhesive, covering the surface of a support sheet, which comprises:

causing a ball to fall freely, from a standstill, from a predetermined starting point, onto the adhesive surface of the said support sheet placed on a horizontal plane at a predetermined distance from said starting point, and exerting a vertical upwardly directed separating force upon the ball according to a predetermined program so as to successively balance the weight of the ball, overcome the retaining force exerted on the ball by the adhesive and bring the ball back to its initial starting point, the measurement of the adhesive power of the adhesive being a function of the time comprised between the instant when the separating force is initially exerted upon the ball and the instant when the ball returns to its initial starting point.

According to one embodiment of the above process, a predetermined length of time elapses between the instant when the ball falls freely and the instant when the vertical separating force is exerted upon the ball.

According to a further embodiment of the invention, the separating force increases progressively.

According to yet another embodiment of the invention, the variation program of the separating force comprises a first phase, wherein this force varies comparatively rapidly from zero to the value which balances the weight of the ball, then a second phase of slower, substantially linear variation, to a value at least equal to the value which ensures the separation of the ball from the surface of the adhesive.

In a further embodiment of the process according to the invention, the attraction force exerted upon the ball is an electro-magnetic force produced by a coil having a magnetic core through which flows an electric current the strength of which varies in accordance with the predetermined program chosen for the said attraction force, the ball being made from a magnetic material.

The initial starting point of this ball is the position in which the ball is pressed against the coil by magnetic attraction; it is caused to fall by interrupting the current energizing the coil.

The instant of the ball's departure and the instant at which the ball returns to its initial starting position, after having been separated from the adhesive, are determined by allowing or preventing a light beam to reach a photo-electric cell, said light beam passing through the space occupied by the ball when it is in its initial starting position, and said cell being connected to time measuring means.

Experience shows that in this case the values obtained for the adhesive power of the adhesive depend upon the support of the adhesive and, more especially upon the manner in which the support is fixed onto the horizontal plane during the measuring operation. In point of fact, when the ball, lying on the adhesive sheet, is submitted to an attraction force, which tends to bring it back to its initial starting position, the support of the adhesive tends to leave the horizontal plane, which results in a deformation entailing a modification of the measured adhesive power values.

The present invention is aimed at rendering the results of the measurements of the adhesive power of an adhesive independent from the support of this adhesive, in the process according to the invention said supporting sheet is applied to said horizontal plane by means of a decreased pressure applied to the under-side of this sheet through small diameter passages provided in the said plane.

Another object of the invention is to provide a device for carrying out said process, in which an electro-magnet adapted to retain, release and attract the ball according to the different steps of the process is placed vertically above the horizontal plane which is adapted to receive the adhesive-covered sheet.

In one embodiment, this device contains a base-plate traversed by small diameter passages provided in its central zone, the top surface of this base-plate forming a horizontal plane adapted to receive the support sheet of the adhesive and the bottom surface of the said base-plate being connected to a tight end-seal which surrounds the said central zone and is in turn connected to a depression source.

Other aims and advantages of the present invention will become evident in the following non-limiting examples and appended drawings.

Figure 1:
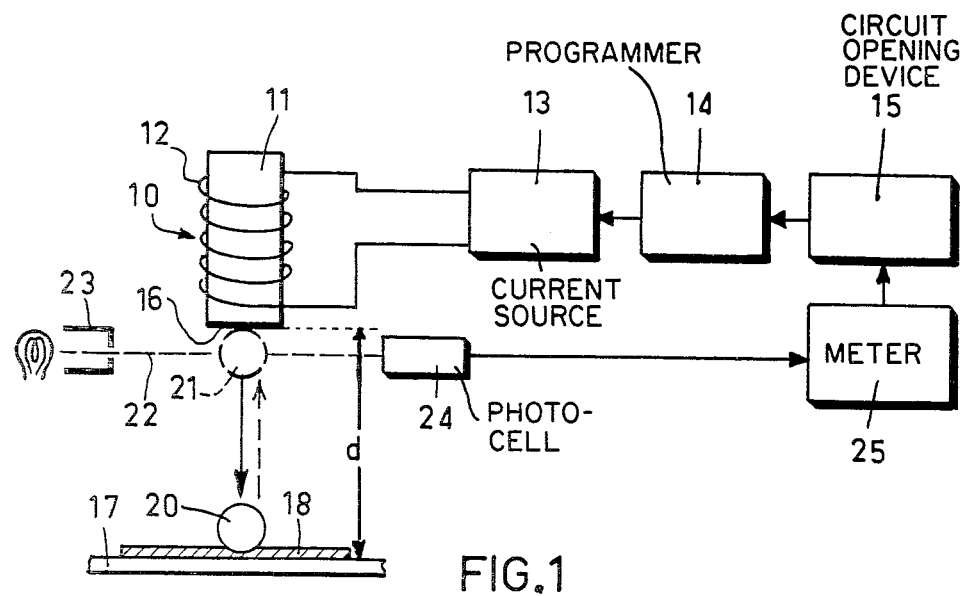
FIG. 1 is a schematic view of one embodiment of the device for implementing the process according to the invention.

In the embodiment of FIG. 1, the device, adapted to be used according to the invention, essentially comprises an electro-magnet 10 with a core 11 having a vertical axis, and a coil 12, the latter being connected to a current source 13 which supplies a controllable energizing current to said coil. This current source is controlled by a programmer 14, adapted to control the value of the energizing current according to a predetermined program, this program being in turn controlled by a circuit opening device 15 whose functioning will be explained hereinafter.

Horizontal plane or base plate 17 is placed at a distance d from the inside surface 16, directly below core 11. Support 18 of the adhesive to be tested is placed on said plane 17, the adhesive surface being turned upwards.

The ball 20, used during the tests, is made from a magnetic material, steel for example, and, in its initial starting position 21, is pressed up against the inside surface of the core of the electro-magnet, the coil of the latter being traversed by a current which is sufficient to maintain the ball in this position.

The device comprises means for detecting if the ball is in its starting position. To this end, the ball in its starting position blacks out beam 22 emitted from source 23 towards photo-electric cell 24 which is connected to measuring device 25 which monitors circuit opening device 15.

Figure 2:
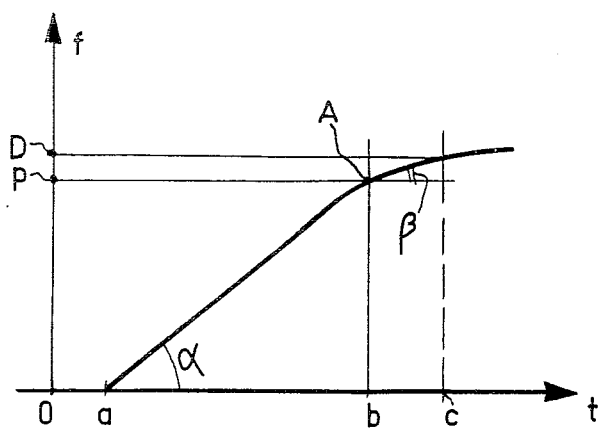
FIG. 2 is a graph illustrating the force exerted upon the ball as a function of time.

The device functions in the following manner: ball 20 occupies its starting position 21; due to a pulse from the circuit opening device (for example, hand-operated) programmer 14 cuts the electro-magnet's power-supply, the freed ball 20 falls, without any initial speed, towards base-plate 17 and uncovers cell 24. The latter, struck by beam 22, sends a signal to the counting device or meter. This signal corresponds to the initial time O on the graph of FIG. 2.

As is noted, ball 20 has fallen onto the adhesive under reproducible conditions. Then, after a predetermined length of time, (0a on the graph of FIG. 2), programmer 14 causes power supply 13 to deliver a progressively increasing electric current in coil 12. The electro-magnet exerts an increasing attraction force on the ball. After a certain length of time b, determined by a preliminary calibration, no adhesive whatsoever being present, this attraction force reaches a value equal to weight p of the ball; during this calibration, ball 20 abruptly leaves base-plate 17 when the attraction force reaches this value p. A relatively large force or current variation as a function of time (angle α of the graph) is selected for this first phase of the electric current establishment program. Then, from the instant b, (which corresponds to point A on the graph), the program is adjusted to transmit a weaker variation pace to the current, thus to the force, as a function of time, (β angle). Thus, from this instant b, the electro-magnet exerts an attraction force upon the ball which is stronger than the weight of the ball. The adhesion power alone prevents the ball from rising until the attraction force reaches a value D corresponding to a separating force which is sufficient to overcome the resistance opposed by the adhesive. Ball 20 goes back up into contact with the electro-magnet and assumes its initial starting position, thus blacking out beam 22 and photo-electric cell 24, which causes the emission of a signal, (corresponding to instant c), towards meter 25.

The programmer 14 may comprise a conventional motor-driven cam having adjacent switches for controlling the desired ramp functions, such as the timers employed for control of house-hold washing machines, dishwashers and similar appliances. Alternatively, a conventional analog or digital function generator may be employed to produce the time-dependent function shown in FIG. 2.

The time which separates the instants b and c is a function of the adhesion power and the stronger the power the greater the lapse of time.

Also, the smaller the angle β the greater the lapse of time; the accuracy of the measurement is improved when this angle is reduced.

The value $D-p$ measures the adhesive force or the instant adhesive power of the adhesive. Experience shows that the results obtained are very easy to reproduce, (i.e. highly consistent).

It will be noted that among the various parameters used in the process according to the invention, some are fixed and predetermined by construction features, such as the weight of the ball, the distance which separates the ball's initial starting position from the horizontal plane, the contact time 0a of the ball with the adhesive; others are adjustable and measured, such as the current circulating in the coil; still others are related to the sample to be measured, especially the weight per area unit or the thickness of the adhesive layer.

The adhesive's resistance to flow can also be evaluated by the process and device according to the invention.

A fixed current intensity is sent to the electro-magnet causing an instantaneous and constant magnet attraction force of a value comprised between the weight of the ball and the separating force D as previously determined. The time it takes to separate the ball is measured; it takes longer than the length of time which was previously determined. Experience shows that this type of measurement is extremely reproducible.

The weight per area unit of the adhesive can also be determined.

A certain adhesive thickness, corresponding to the definition of the weight per area unit, is applied to the support of the adhesive tape.

When the ball falls it sinks into the adhesive layer. The releasing force will be proportional to the weight per area unit for given operating conditions and for the same type of adhesive and adhesive tape support.

Thus a calibration curve can be constructed, on a production unit, giving the releasing force in function of the weight per area unit, a quick measuring of the force during the manufacturing process of the adhesive tape will give the weight per are unit.

Figure 3:
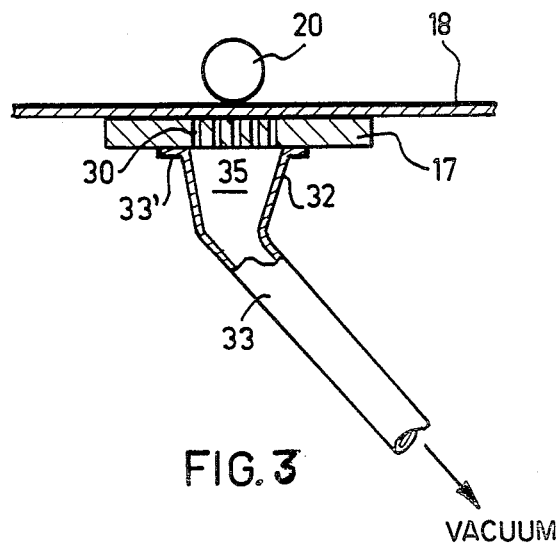
FIG. 3 is a cross-sectional view of a plate, its upper surface constituting the plane which receives the support of the adhesive to be measured; this plate is fitted out with holding means for the support according to the invention.
Figure 4:
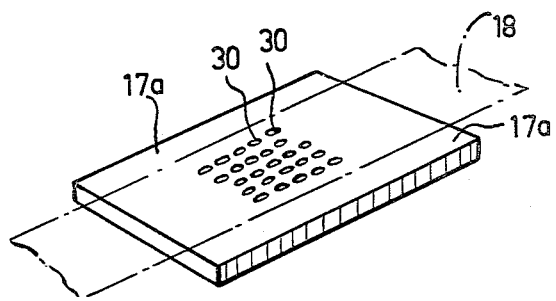
FIG. 4 is a schematic view, from above, of the plate of FIG. 1.

In another embodiment of the invention, represented in FIGS. 3 and 4, the upper surface of base-plate 17a forms the plane adapted to receive imperforate adhesive support 18; this base-plate is pierced, in its central zone, by a series of holes 30 traversing it. The bottom surface of base-plate 17a is connected to the end 32 of tubulure 33 which surrounds the pierced zone of said base-plate, and is connected by annular flange 33' to this surface; tubulure 33 communicates with a vacuum source, (not shown); thus it is possible to create in chamber 35, formed by said flange 33' and base-plate 17, a vacuum which tends to flatten, against said base-plate 17a, support 18 covered with the adhesive whose adhesive power is to be measured.

Therefore, the support is uniformly fixed to the measuring plane and thus the value of the measurement is not interfered with. In other words, support 18 remains in contact with the measuring plane, that is to say, with the upper surface of base-plate 17a for the whole time during which the electro-magnet exerts separating force 20, which in turn is exerted upon the ball, without said support 18 being able to deform itself by following the ball during this releasing phase.

Experience proves that the measurements of a given adhesive's adhesion power are accurate and practically independent of the nature of the support used.

Naturally the invention is not limited to the embodiments and examples described hereinabove. Many variants and modifications can be envisaged by those skilled in the art, without departing from the spirit and scope of the invention as defined in the appended claims.

What is claimed is:

1. A method for determining the adhesive power of a supported pressure sensitive adhesive which comprises:
    (a) dropping a ball from a predetermined starting point at a given time, onto the surface of a pressure sensitive adhesive coated support, placed in a horizontal plane at a predetermined distance below the starting point, to cause said ball to become adherent to said adhesive;
    (b) subsequently applying a preprogrammed vertical, upwardly directed monotonically increasing separating pulling force at a first rate to the ball to successively balance the weight of the ball, and thereafter at a second rate less than said first rate to overcome the adhesion force exerted by the adhesive and return the ball to the initial starting point thereof at a subsequent time, the adhesive power of said adhesive being a function of the time interval between the dropping of the ball and return of the ball to said initial starting point; and
    (c) generating a signal having a value corresponding to the interval between said given and subsequent times.

2. A process according to claim 1, wherein said support is a sheet maintained in said horizontal plane, by means of vacuum produced under the sheet through small diameter passages provided in a planar surface.

3. A process according to claim 1, wherein a predetermined length of time elapses between the instant when the ball is released and the instant when the vertical separating force is exerted upon the ball.

4. A process according to claim 1, wherein the attraction force exerted upon the ball is an electro-magnetic force produced by a coil with a magnetic core.

5. A process according to claim 1, wherein the instant of the ball's departure and the instant at which the ball returns to its initial starting point, after having been separated from the adhesive are determined by the switching on or off of a luminous beam directed towards a photo-electric cell through the volume which the ball fills when it is at its initial starting point, said cell being connected to time measuring means.

6. A process according to claim 1, wherein an attractive separating force, slightly stronger than the weight of the ball, is substantially instantaneously applied to the ball.

7. A process according to claim 6, wherein the initial starting point of the ball is the location in which the ball is pressed against the core by magnetic attraction, its fall being caused by cutting off the energizing current of the coil.

8. A device for determining the adhesive power of a pressure-sensitive adhesive comprising a current source, an electromagnet placed above a horizontal plane adapted to receive an adhesive-covered sheet, said electro-magnet comprising a coil connected to said current source for generating an electromagnetic field having a strength corresponding to the current provided by said source, a programmer for varying the current provided by said current source, a circuit opening device for controlling said programmer, means for selectively operating said circuit opening device to cause said electromagnet to attract said ball so that said ball is suspended above said plane, and so that said ball is dropped onto said sheet at a desired time, a ball made of magnetic material placed under the electro-magnet and above the plane, means for detecting that said ball is at an initial starting point thereof and adjacent the electro-magnet, a time interval measuring device connected to said detecting means, and means enabling said detecting means to control the circuit opening device to change the current provided by said source.

9. A device according to claim 8, further comprising a base-plate having a central zone traversed by small diameter passages therein, the top surface of said base-plate forming a horizontal plane adapted to receive a support sheet of the adhesive and the bottom surface of the base-plate being connected to a conduit, one end of said conduit communicating with said central zone, and means for coupling the other end of said conduit to a vacuum source.

10. A method for determining the adhesive power of a pressure-sensitive adhesive supported on a horizontal surface, comprising the steps of:
    mounting an electro-magnetic coil having a magnetic core at a predetermined distance above said adhesive;
    positioning a ball of magnetic material adjacent said core, and applying a current to said coil to exert a magnetic attraction force upon said ball to retain said ball in position;
    causing said current to decrease, to reduce the magnetic attraction between said ball and said core, allowing said ball to fall onto said adhesive;
    applying a vacuum to the lower surface of a base-plate having through-holes therein, the upper surface of said base-plate having the supported adhesive disposed thereon, said vacuum tending to flatten said adhesive against said base-plate;
    after the ball falls onto said adhesive, and after said vacuum applying step, applying an increasing current to said coil to increase the magnetic attraction force between said ball and said core to a value sufficient to cause said ball to be detached from said adhesive and returned to the initial position thereof adjacent said core; and
    photoelectrically determining the time between the departure of said ball from the initial position thereof adjacent said core, and the return of said ball to said initial position, by measuring the time interval during which a light beam traversing said ball is not intercepted thereby.

* * * * *

UNITED STATES PATENT OFFICE
CERTIFICATE OF CORRECTION

Patent No. 4,194,392          Dated  March 25, 1980

Inventor(s)   Serge Lombard, et al

It is certified that error appears in the above-identified patent and that said Letters Patent are hereby corrected as shown below:

Column 4, line 47: "are" should be --area--.

Signed and Sealed this

Twelfth Day of August 1980

[SEAL]

Attest:

SIDNEY A. DIAMOND

*Attesting Officer*          *Commissioner of Patents and Trademarks*